(12) United States Patent
Uppugunduri

(10) Patent No.: US 7,687,476 B2
(45) Date of Patent: Mar. 30, 2010

(54) SPECIFIC INHIBITORS OF ACUTE AND CHRONIC INFLAMMATION

(76) Inventor: Srinivas Uppugunduri, S-589 51, Linköping (SE)

( * ) Notice: Subject to any disclaimer, the term of this patent is extended or adjusted under 35 U.S.C. 154(b) by 940 days.

(21) Appl. No.: 10/994,663

(22) Filed: Nov. 22, 2004

(65) Prior Publication Data

US 2005/0090467 A1 Apr. 28, 2005

Related U.S. Application Data

(63) Continuation of application No. 09/986,522, filed on Nov. 2, 2001, now abandoned.

(51) Int. Cl.
*A61K 31/7072* (2006.01)
*A61K 31/513* (2006.01)

(52) U.S. Cl. .................... 514/49; 514/269

(58) Field of Classification Search .............. 514/49, 514/269
See application file for complete search history.

(56) References Cited

U.S. PATENT DOCUMENTS

| | | | | |
|---|---|---|---|---|
| 3,865,957 A | * | 2/1975 | Schieweck et al. | 426/548 |
| 3,940,481 A | * | 2/1976 | Schiweck | 514/23 |
| 5,190,948 A | * | 3/1993 | Materazzi et al. | 514/274 |
| 5,378,693 A | * | 1/1995 | McCarthy et al. | 514/45 |
| 5,470,838 A | * | 11/1995 | von Borstel et al. | 514/50 |
| 5,538,854 A | * | 7/1996 | Faustman | 435/7.24 |
| 5,567,689 A | * | 10/1996 | Sommadossi et al. | 514/50 |
| 5,583,117 A | * | 12/1996 | von Borstel et al. | 514/50 |
| 5,607,925 A | * | 3/1997 | Matthews et al. | 514/45 |
| 5,646,182 A | * | 7/1997 | Burzynski | 514/532 |
| 5,691,320 A | * | 11/1997 | von Borstel et al. | 514/50 |
| 5,753,625 A | * | 5/1998 | Buelow | 514/13 |
| 5,958,897 A | * | 9/1999 | Jacobus et al. | 514/49 |
| 5,962,459 A | * | 10/1999 | Piazza et al. | 514/269 |
| 5,985,849 A | * | 11/1999 | Kindon et al. | 514/51 |
| 6,329,350 B1 | * | 12/2001 | von Borstel et al. | 514/50 |
| 6,403,565 B1 | * | 6/2002 | von Borstel et al. | 514/45 |
| 6,673,606 B1 | * | 1/2004 | Tennekoon et al. | 435/372 |
| 6,800,469 B1 | * | 10/2004 | Conrad et al. | 435/194 |

FOREIGN PATENT DOCUMENTS

| EP | 0462075 | 12/1991 |
|---|---|---|
| JP | 3135918 | 5/1991 |
| WO | 8903837 | 5/1989 |
| WO | 9426280 | 11/1994 |
| WO | WO 9601115 | 1/1996 |
| WO | WO 9413687 | 6/1997 |

OTHER PUBLICATIONS

Simone, Oncology: Introduction, Cecil Textbook of Medicine 20th Edition, vol. 1, pp. 1004-1010, 1996.*
Kansas, G., "Selectins and Their Ligands: Current Concepts and Controversies," *J. American Society of Hematology*, vol. 88, n. 9 (Nov. 1, 1996): 3259-3287.
McEver, R.P., "Selectin-carbohydrate interactions during inflammation and metastasis," *Glycoconjugate Journal*, (1997) 14: 585-591.
Springer, T.A., "Traffic Signals for Lymphocyte Recirculation and Leukocyte Emigration: The Multistep Paradigm," *Cell*, vol. 76, 301-314, Jan. 28, 1994.
"4-Thiouridine Incorporationg into the RNA Monkey Kidney Cells (CV-1) Triggers Near-UV Light Long Term Inhibition og DNA, RNA, and Protein Synthesis," Favre et al. *Photochemistry and Photobiology*. 1993. vol. 58, No. 5.
"A 5-4 Pyrimidine-Pyrimidone Photoproduct Produced from Mixtures of Thymine and 4-Thiouridine Irradiated with 334nm Light," Blazek et al. *Photochemistry and Photobiology*. 1993. vol. 57, No. 2.
"tRNA$^{Phe}$ and tRNA$^{Pro}$ Are the Near-Unltrviolet Molecular Targets Triggering the Growth Delay Effect,"Blondel et al. *Biochemical and Biophysical Research Communications*. 1988. vol. 150. No. 3.
"Detection of Pseudouridine and other Modifications in tRNA by Cyanoethylation and MALDI mass Spectrometry," Mengel-Jorgensen et al. *Nucleic Acids Research*. 2002. vol. 30, No. 23.
"Effect of Uridine Supply on Glycogen Resynthesis After Ischaemia in the Isolated Perfused Rat Heart" J. Aussedat; Cardiovasic Research; Mar. 1993, vol. 17; pp. 145-151.
Farmakol Toksikol, 20, (2) pp. 200-202. (English Abstract) Mar.-Apr. 1977, Bushma et al., Pharmacology uridine and cytidine.

* cited by examiner

*Primary Examiner*—Brian-Yong S Kwon
(74) *Attorney, Agent, or Firm*—Gauthier & Connors LLP

(57) ABSTRACT

The present invention relates to the use of one or more of the compounds of the group consisting of 4-thiouridine, isomaltitol, and uridine in the preparation of therapeutically effective compositions against acute or chronic inflammations, and/or problems in hemostasis related to platelet function, as well as a method for treatment of acute or chronic inflammations, and/or problems in hemostasis related to platelet function with the exception of the use of uridine in the treatment of inflammatory conditions caused by a bacterial infection.

4 Claims, 10 Drawing Sheets

SPECIFIC INHIBITORS OF ACUTE AND CHRONIC INFLAMMATION

PRIORITY INFORMATION

Figure 1:
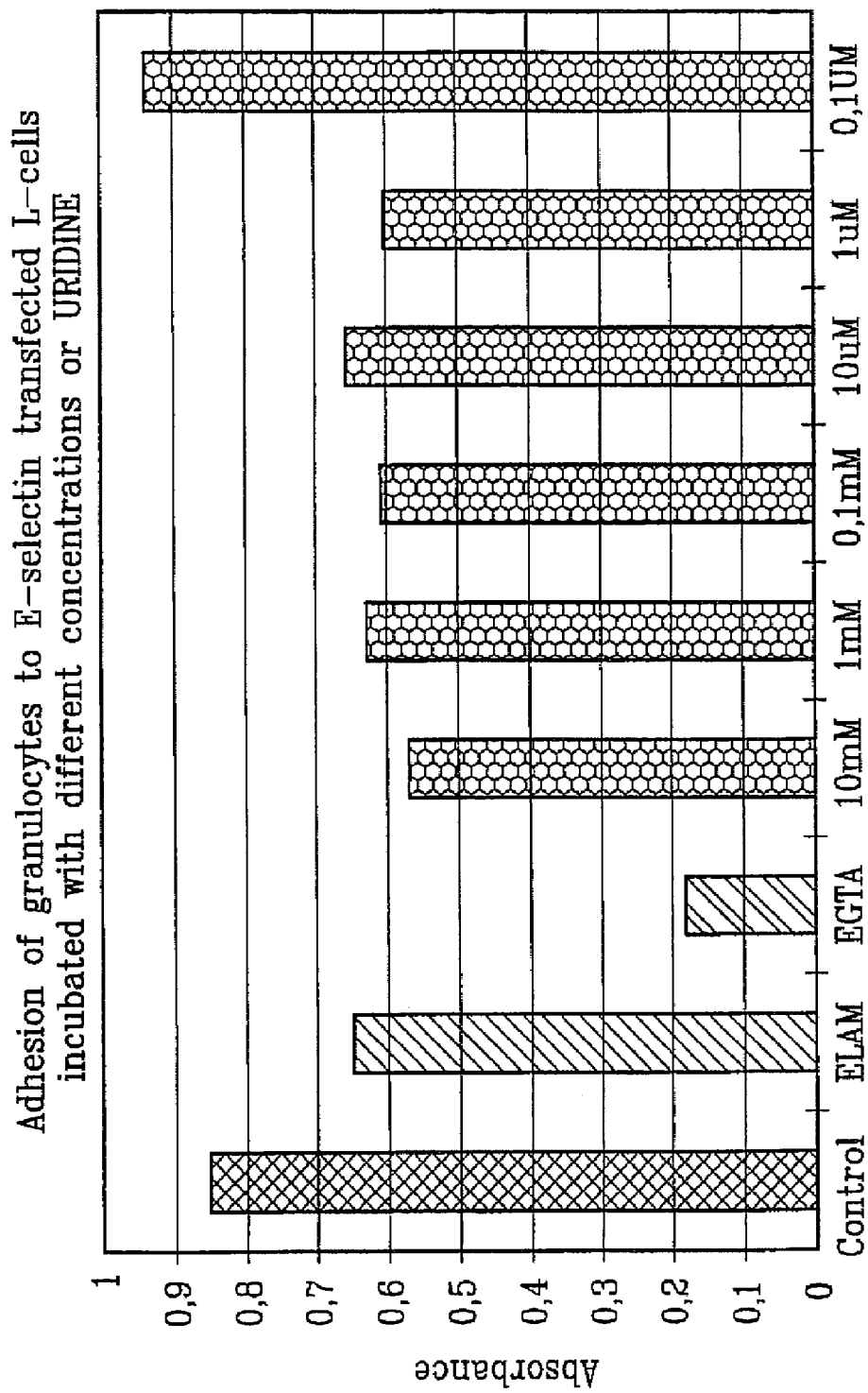

This application is a Continuation of U.S. Ser. No. 09/986,522, filed Nov. 2, 2001 now abandoned.

TECHNICAL FIELD

The present invention relates to novel, specific inhibitors of acute and chronic inflammation, method for treatment of acute and chronic inflammation and/or problems in hemostasis related to platelet function.

The object of the present invention is to obtain novel, specific inhibitors of acute and chronic inflammations in order to be able to treat such inflammations.

BACKGROUND OF THE INVENTION

Three families of cell-adhesion molecules (CAMs) have been implicated in mediating interactions of platelets, endothelial cells, and leukocytes: the selectins, the integrins and the immunoglobulin superfamily. The selectin family of molecules comprising E-, L-, and P-selectin act in concert with other cell adhesion molecules to effect adhesive interactions of platelets, endothelial cells, and leukocytes. Extensive literature is available implicating cell adhesion molecules in diverse disease processes including reperfusion injury, cancer, coronary heart disease, atherosclerosis, restenosis after coronary angioplasty, and chronic inflammatory diseases like asthma and IBD.

The emigration of white blood cells to inflammatory sites requires at least four steps: leukocyte rolling along activated endothelium, leukocyte activation, firm adhesion and transendothelial migration. Interaction of the selectins with their carbohydrate ligands seems to be important for the initial binding of the leukocytes to the endothelium under conditions of fluid shear stress. Subsequent firm adhesion and extravasation seems to be mediated by another family of molecules, the β2 (CD 18)-integrins. A number of soluble mediators like IL-1β, TNF, endotoxin, thrombin and histamine can up regulate one or more endothelial adhesion molecules. The major adhesion receptors and ligands regulating leukocyte-endothelium interactions include ICAM-1, ICAM-2/LFA-1; VCAM/VLA-4; L-selectin/GlyCAM-1; CD 34, MAdCAM-1; E-selectin/ESL-1, PSGL-1; P-selectin/PSGL1

Genetic experiments involving construction and testing of mice deficient in each of these selectins suggest that they provide overlapping, but crucial contributions to leukocyte recruitment in inflammation. Mice lacking each of these selectins exhibit defects in neutrophil rolling and extravasation. Further, mice deficient in both E and P selectin present extreme leukocytosis, elevated cytokine levels and alterations in haematopoesis.

Platelet P-selectin may also play a very important role in both hemostasis and the ensuing inflammatory reaction. Platelets are rapidly recruited to the site of the vascular injury to prevent excessive bleeding. The interaction of platelets with the vessel wall is a crucial event leading to the formation of a hemostatic plug. The role of platelet P-selectin in hemostasis was confirmed in a recent study which showed that platelets roll on stimulated endothelium expressing P-selectin in vivo. Furthermore, bleeding time was prolonged by 40% in P-selectin deficient mice.

Today the treatment of inflammatory conditions include treatment using steroids which negatively affect the immuno defence system and leads to a total inhibition of the inflammation, where it is of interest and importance to control the inflammatory regulating system.

WO 96/01115 relates to pyrimidine nucleotide precursors for treatment of systemic inflammation and encompasses uridine. The systemic inflammations are caused by bacterial sepsis.

Inflammation is a common feature in the pathogenesis of numerous diseases. Inflammation is normally localized defensive response to invasion of the host by foreign material. Inflammation can be caused by a wide variety of agents including mechanical trauma, toxins, and neoplasia and is not a response reserved exclusively for basal infections. The accumulation and subsequent activation of leukocytes are, however, central events in the pathogenesis of virtually all forms of inflammation.

The knowledge of a protective effect of uridine in bacterial sepsis does not automatically lead to the deduction that uridine could benefit in inflammation caused by other agents. Similarly, although it is known that bacterial sepsis can lead to coagulation problems, a number of bleeding disorders are associated with platelet dysfunction without a concomitant bacterial infection. Since bacteria are not involved in the etiology of a number of diseases. covered by the present use including reperfusion injury, cancer, coronary heart disease. arteriosclerosis, restenosis after coronary angioplasty, and chronic inflammatory diseases like asthma, rheumatoidal diseases like rheumatoid arthritis, and IBD.

Rational Behind Random In Vitro Screening

Since initial binding of leukocytes to endothelium initiates the inflammatory process, it has been utilised in an vitro system to study the adhesion of various cells to human umbilical cord endothelial cells. The method is well established and has been successfully utilised by a number of research groups. This in vitro static adhesion assay has been used herein for random screening of substances that can block leukocyte adhesion to endothelial cells. A variety of substances were tested as literature has shown that a number of, both, carbohydrate and non-carbohydrate structures can block interaction of selectins with cognate ligands. Substances that can block interaction of endothelial adhesion molecules with cognate ligands on leukocytes have potential as novel, selective inhibitors of acute and chronic inflammatory reactions and ischemia reperfusion states, without risk of general immuno suppression.

DESCRIPTION OF THE PRESENT INVENTION

Random screening of various chemical entities resulted in identification of three lead compounds that could block adhesion of neutrophils. The compounds obtained in this screening were: isomaltitol, uridine and 4-thiouridine.

The invention will be described more in detail in the following with reference to screening tests performed. The test results are also illustrated in the accompanying graphs.

The Results of the Screening of Substances that can Block Adhesion of Neutrophils to L-Cells Transfected with E-Selectin L-cells permanently transfected with full-length E-selectin by electroporation. Human neutrophils were isolated from EDTA whole blood by density centrifugation. Purity and total number were determined by standard haematology instruments, L-cells were grown in 96-well microtiter plates.

L-cells and neutrophils were pre-incubated with respective substances for 45 min at 37° C. Neutrophils were then allowed to adhere to L-cells in the presence of different substances for 20 min at 37° C. Non-adherent cells were removed by repeated washings and the number of adherent cells determined by measuring myeloperoxidase content. Since binding of neutrophils to selectin is calcium dependent, EGTA (which chelates calcium) was used as a negative control.

Figure 2:
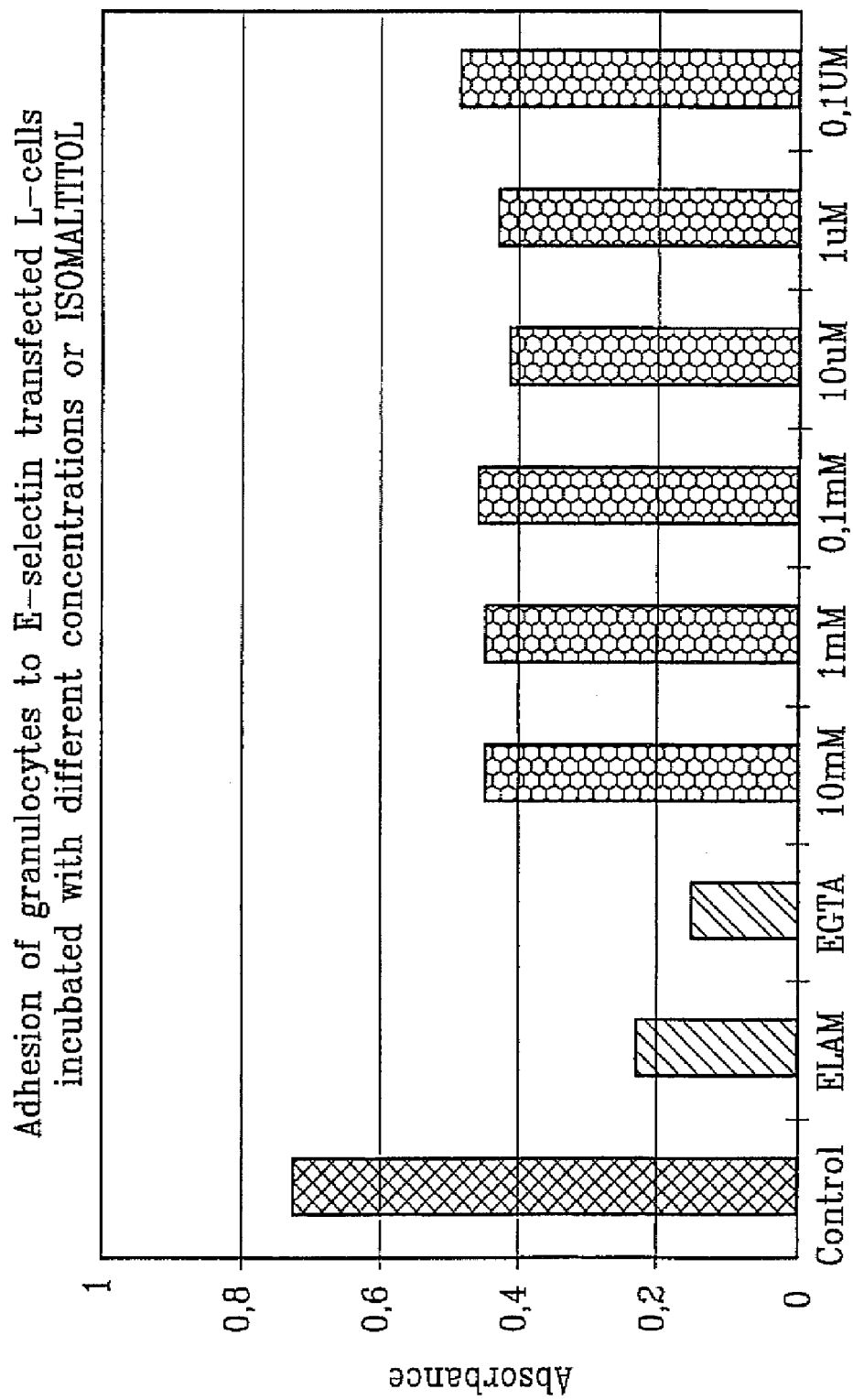
Figure 3:
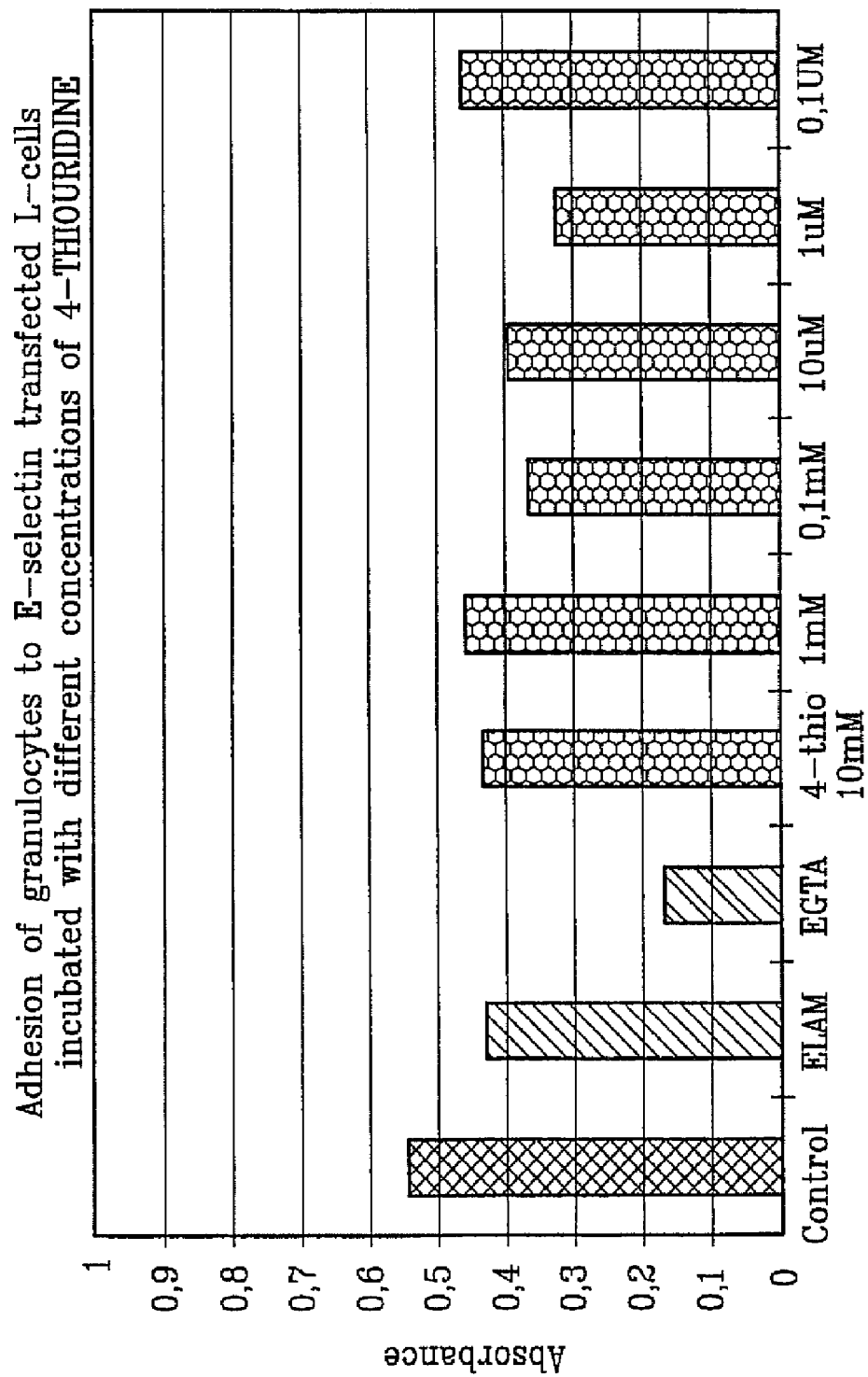

All three substances inhibit adhesion of neutrophils, but to different extents (FIG. 1-3). EGTA consistently blocks adhesion of neutrophils. There is no clear dose-response for these substances which could partly depend on the fact that this is a static adhesion assay and select mediated binding seems to function best under flow conditions. Maximal inhibition seemed to occur already at micromolar levels.

Random Screening of Substances that can Block Adhesion of Colon Cancer Cells, Colo 201, to L-cells Transfected with E-Selectin Although protein ligands have been characterised for the selectins, they recognise a number of carbohydrate and non-carbohydrate ligands. The hypothesis is that these compounds should block E-selectin-SLe$^x$ interaction. To confirm this it was also tested if these substances can block adhesion of Colo 201 cells to L-cells. This interaction has been shown to be mediated predominantly by E-selectin—SLe$^x$ group of molecules.

Figure 4:
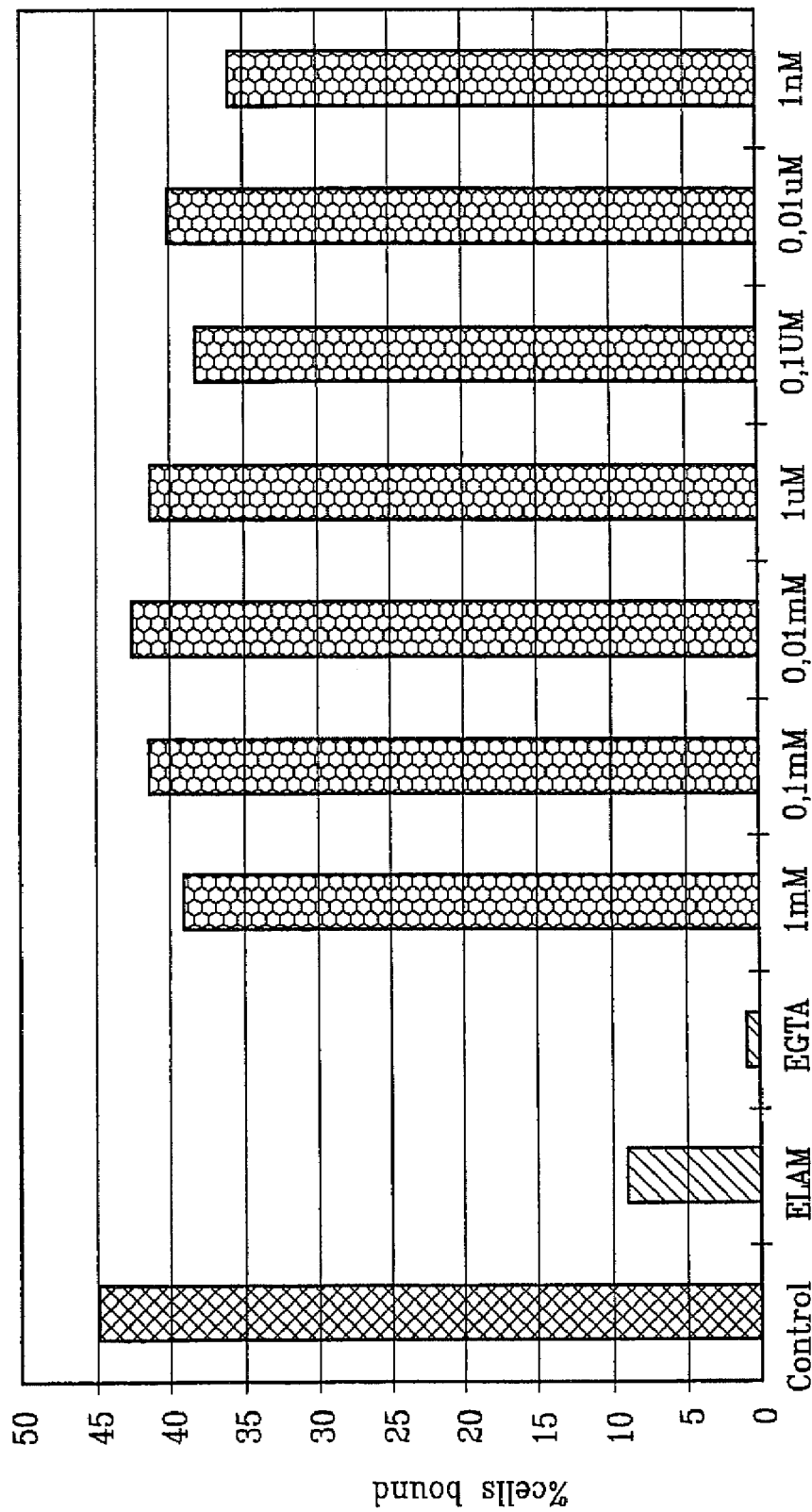
Figure 5:
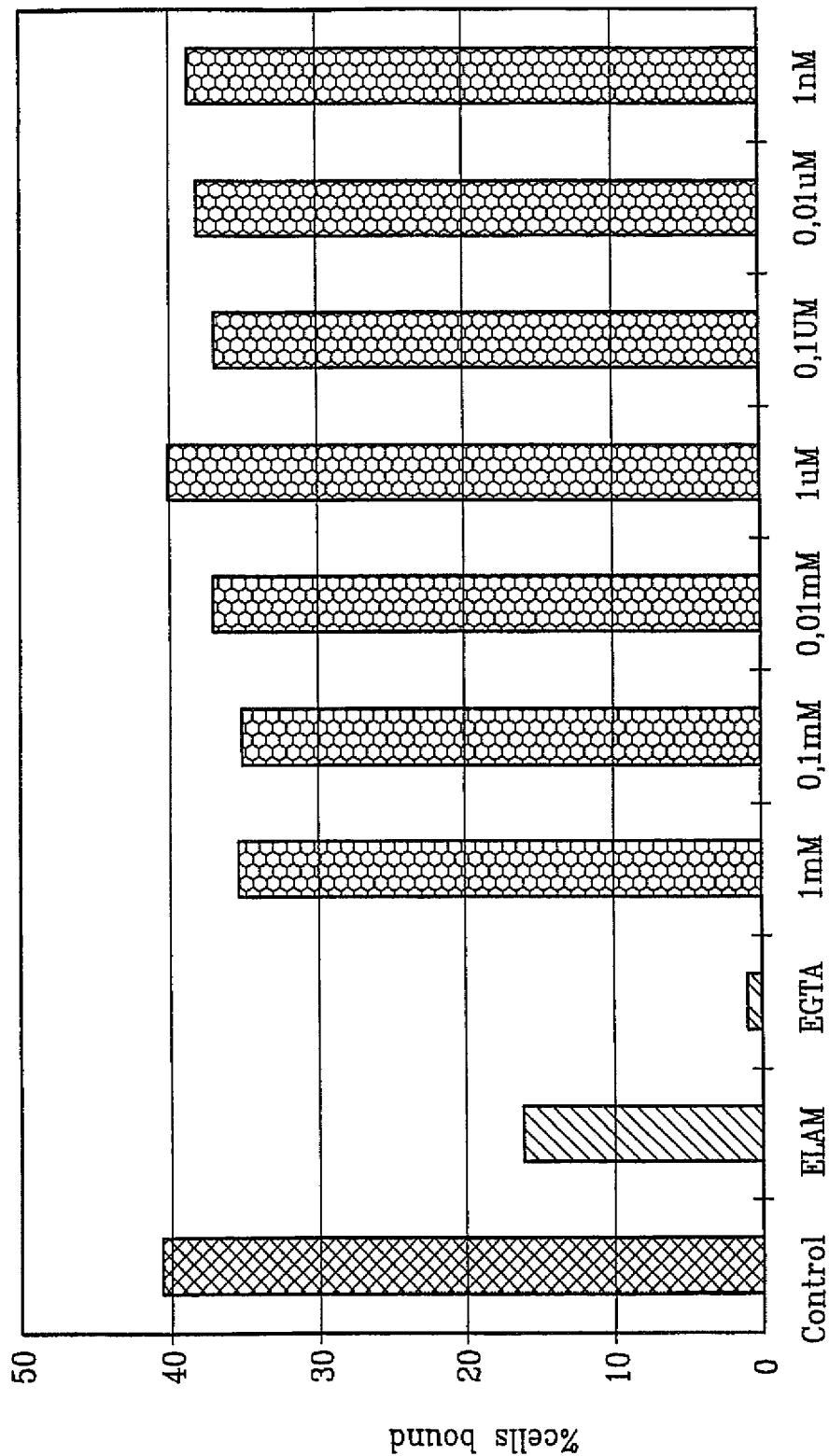
Figure 6:
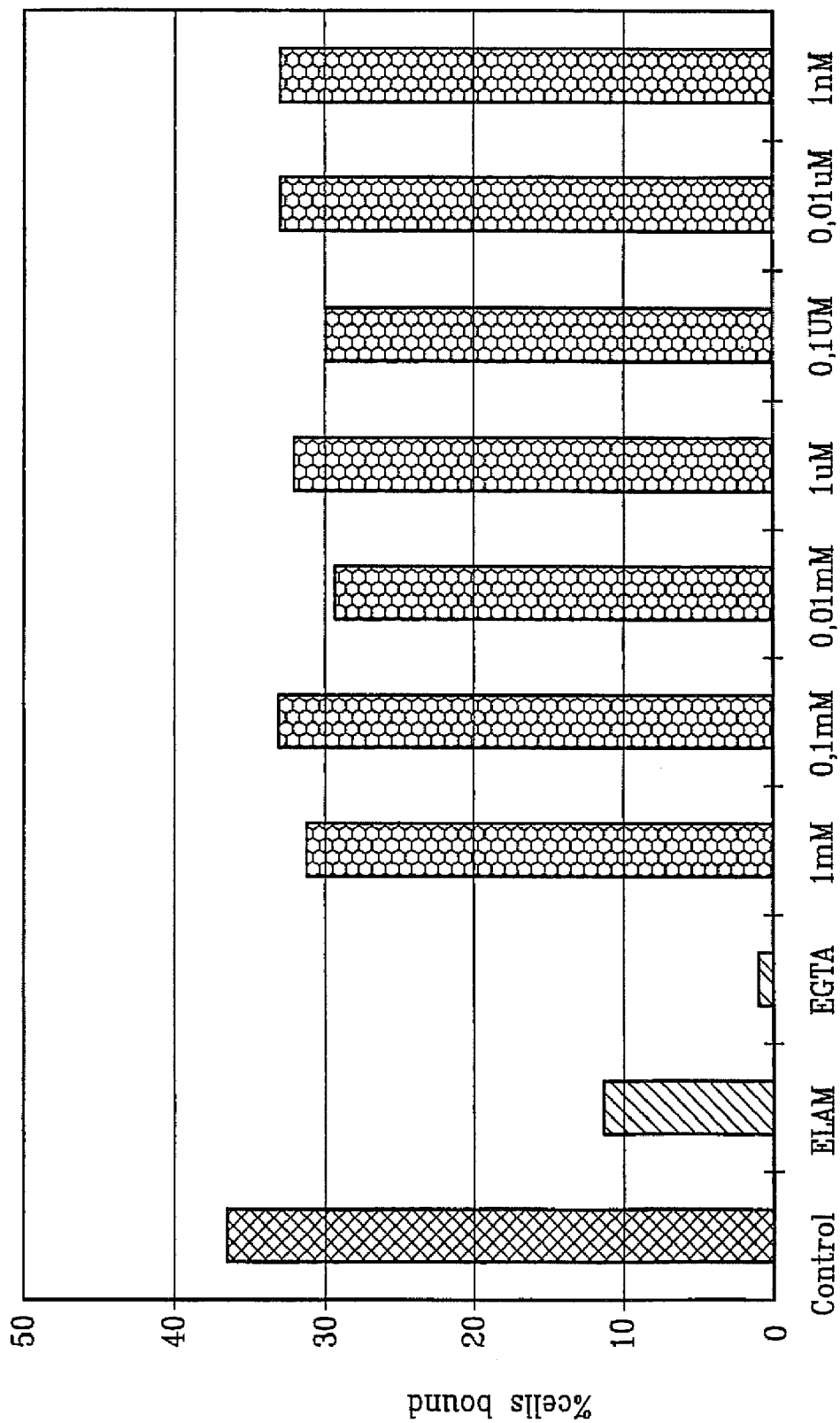

None of these substances could inhibit binding of Colo 201 cells to HUVEC suggesting that this is a specific inhibition of neutrophils (FIG. 4-6). Once again EGTA blocked adhesion of Colo 201 cells. In contrast to previous experiments with neutrophils, a monoclonal antibody against E-selectin was also quite effective in blocking adhesion of Colo 201 cells to TNF stimulated HUVEC.

Inhibition of Neutrophil Adhesion to TNF Stimulated HUVEC

To further extend the finding from L-cells the binding of neutrophils to TNF activated endothelium (HUVEC) was studied.

Endothelial cells were grown in 96-well microtiter plates to confluence. They were stimulated with TNF for 4 h at 37° C. Isolated neutrophils were incubated for 30 min at 37° C. with respective substances. The endothelial cells were washed after 4 h and $2 \times 10^5$ neutrophils were added to each well and the cells were allowed to adhere in the presence of the respective substances.

Figure 7:
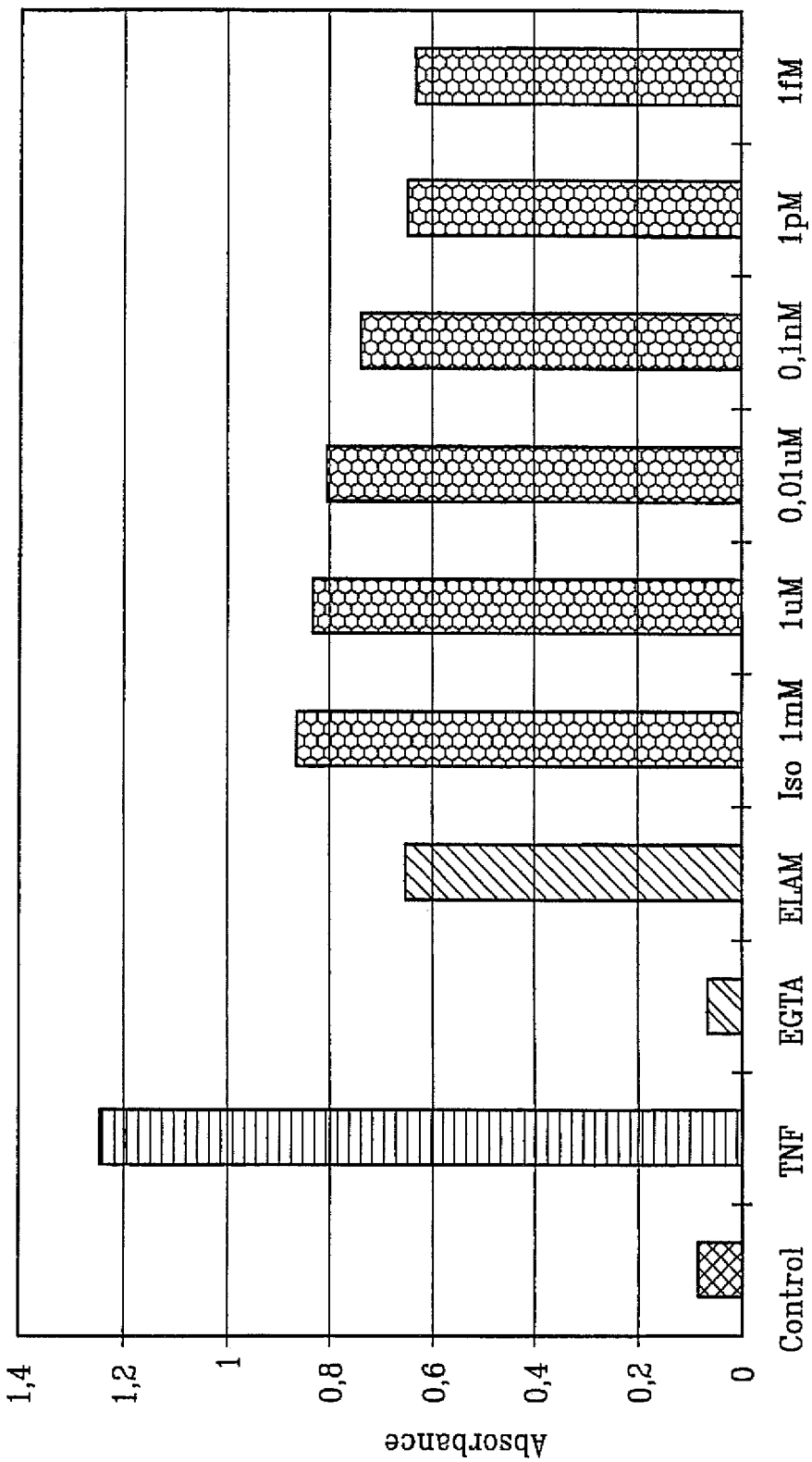

Isomaltitol inhibited the adhesion of neutrophils to TNF stimulated HUVEC by roughly 30%. Once again a clear dose-response was not observed. In fact, the opposite seems to be true with increasing inhibition with decreasing dose (FIG. 7).

Figure 8:
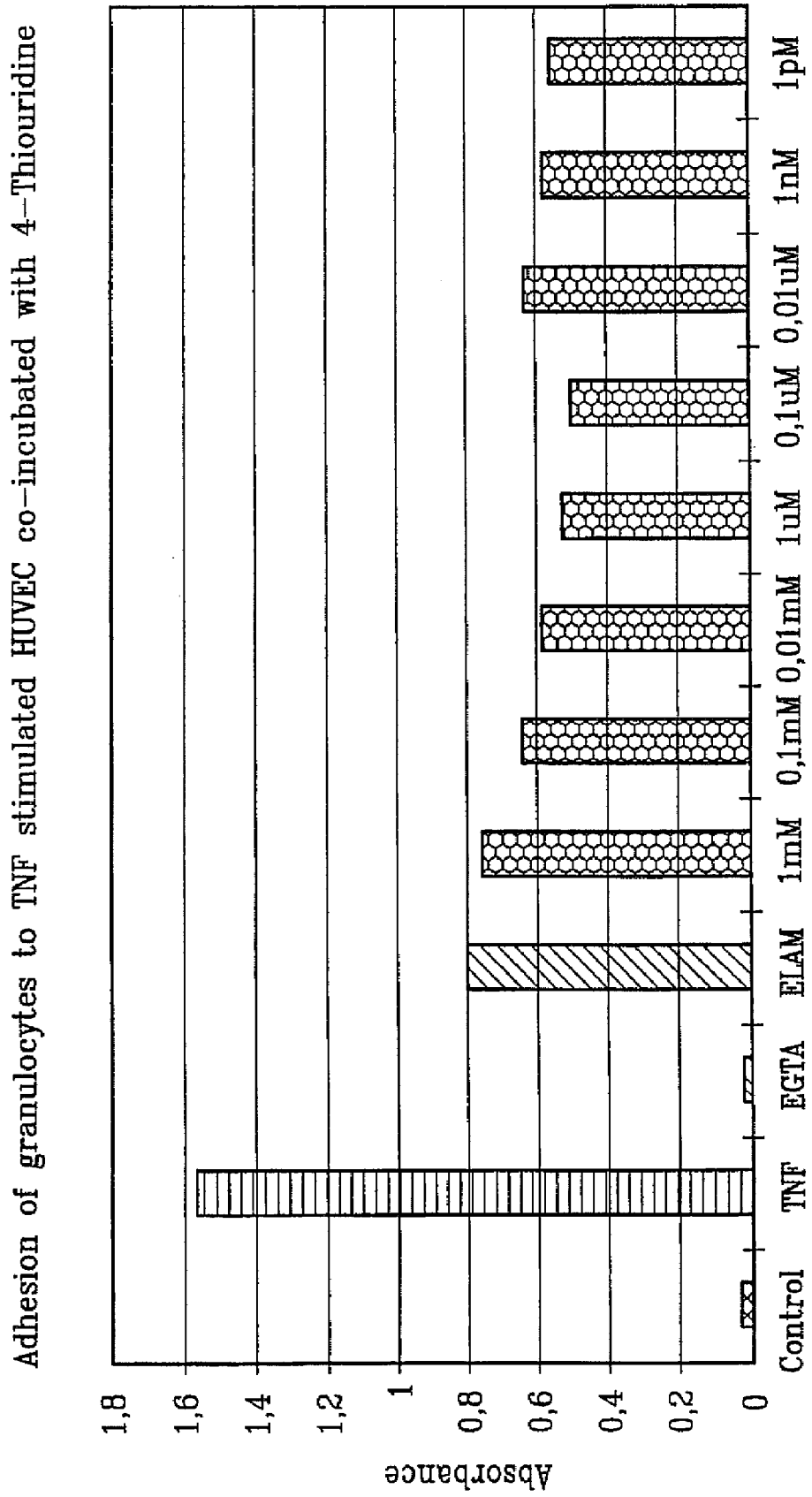
Figure 9:
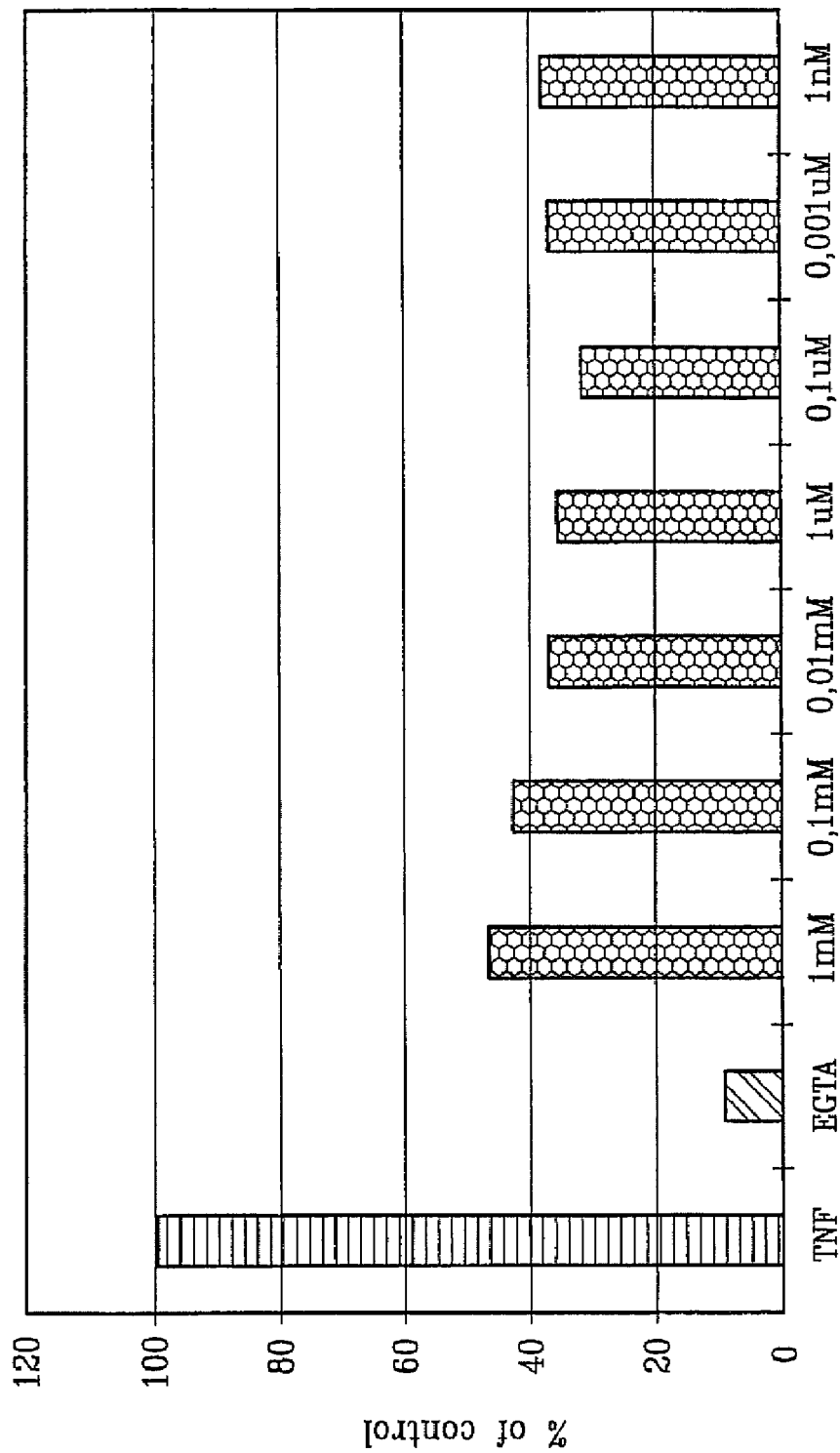

4-Thiouridine was more potent in inhibiting adhesion of neutrophils to TNF stimulated HUVEC. 4-Thiouridine reduced the adhesion of neutrophils by 60%. Maximal adhesion seemed to occur already in the micromolar levels. FIG. 8 shows a representative experiment and FIG. 9 summarises data from two separate experiments performed in quadruplicate. Pre-incubation of neutrophils with EGTA or monoclonal antibodies against E-selectin blocked adhesion of neutrophils.

Effect of 4-Thiouridine on Up-Regulation of E-Selectin

The substances mentioned above should block the interaction of E-selectin with it's ligand and should not have any effect on cytokine induced up-regulation of adhesion molecules. A cell-ELISA was performed to assess the surface expression of adhesion molecules.

Endothelial cells were grown in microtiter plates, stimulated with TNF or IL-1 with or without respective substances for 4 h at 37° C. After stimulation the cells were washed and fixed with formaldehyde. A cell-ELISA was performed in analogy to regular ELISA using primary and secondary antibodies.

Figure 10:
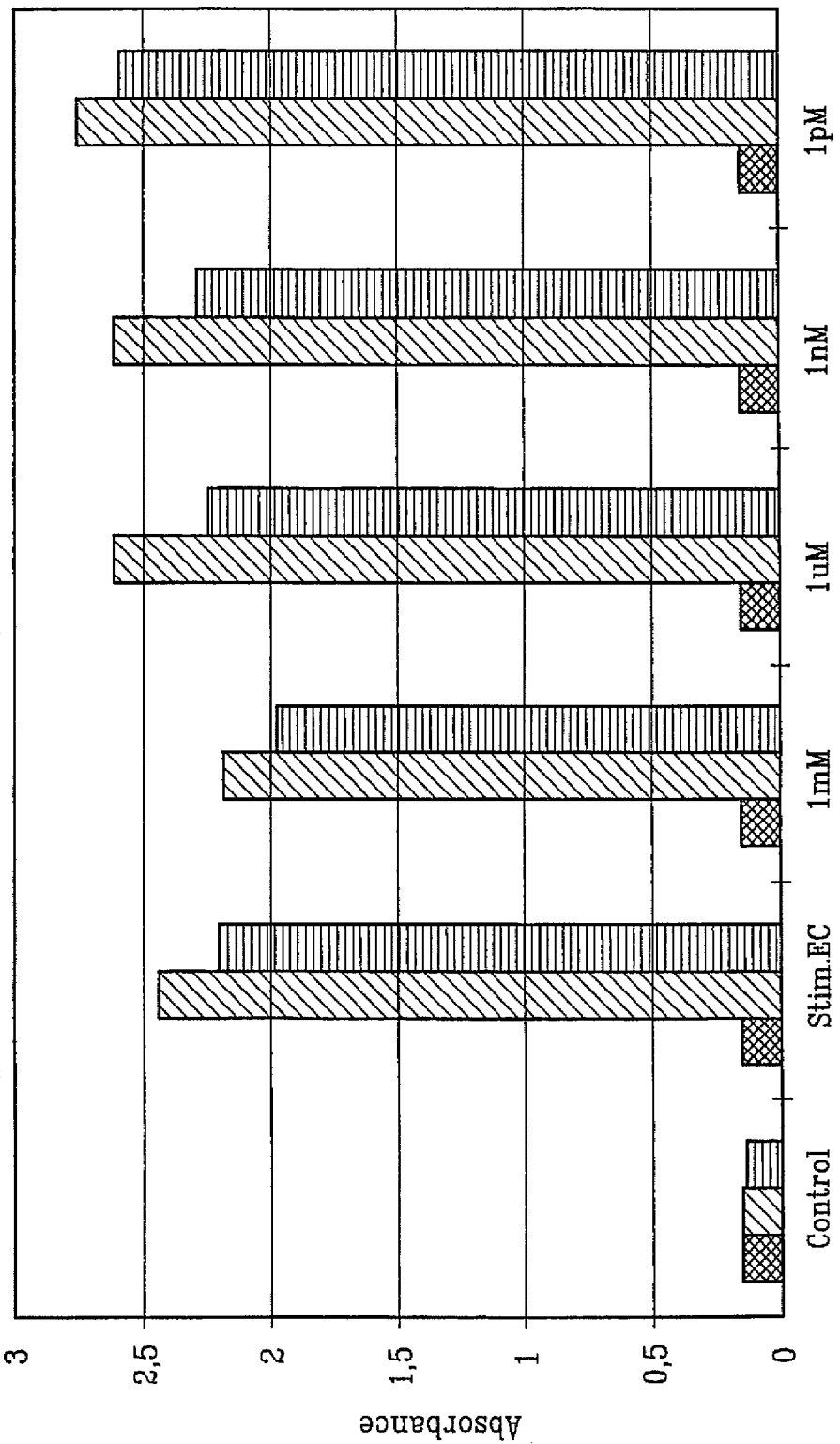

Simultaneous incubation of endothelium with different concentration of 4-thiouridine did not affect TNF induced up-regulation of E-selectin as judged by Cell-ELISA (FIG. 10). These results suggest that 4-thiouridine inhibits neutrophil adhesion by interfering with interaction of E-selectin with cognate ligands and does not seem to affect up-regulation of E-selectin.

Viability

E-selectin transfected L-cells were incubated with 1 mM, 0.1 mM, 0.001 mM, 0.1 µM uridine, thiouridine, or isomaltitol for 2 hours. Viability after incubation was >90%. Similarly neutrophils were incubated with 1 mM, 0.1 mM, 0.001 mM, 0.1 µM uridine, thiouridine, or isomaltitol for 2 hours. Viability after incubation was 80-97%.

Myeloperoxidase Activity

Uridine, isomaltitol and 4-thiouridine do not affect myeloperoxidase activity. Since the number of adherent neutrophils are calculated by measuring neutrophil myeloperoxidase activity, it could be argued that these substances could have a direct effect on myeloperoxidase activity and thus create a methodological artifact. Neutrophils were incubated with different concentrations of uridine, isomaltitol, and 4-thiouridine (100 µM, 10 µM, 1 µM, 100 nM, 10 nM) for 2 hours at 37° C. Incubation of neutrophils with the substance did not affect absorbance due to myeloperoxidase activity.

Effect of Related Substances

L-cells and neutrophils were preincubated with decreasing concentrations of maltose, fucose, and thymidine (1 mM, 10 µM, 0.1 µM, and 1 nM) for 45 min at 37° C. Neutrophils were then allowed to adhere to L-cells in the presence of respective substances for 20 min at 37° C. Non-adherent cells were removed by repeated washings and the number of adherent cells determined by measuring myeloperoxidase content. Maltose, fucose, and thymidine did not affect the adhesion of neutrophils to E-selectin transfected fibroblasts.

Dose Dependent Inhibition Induced by EGTA

L-cells were grown in 96-well microtiter plates. L-cells and neutrophils were preincubated with decreasing concentrations of EGTA (10 mM, 1 mM, 0.1 mM, 10 µM) for 45 min at 37° C. Neutrophils were then allowed to adhere to L-cells in the presence of EGTA for 20 min at 37° C. Non-adherent cells were removed by repeated washings and the number of adherent cells was determined by measuring myeloperoxidase content. It was observed a dose dependent inhibition of neutrophils adhesion to L-cells. Similarly a dose dependent inhibition of neutrophils adhesion to activated HUVEC was observed.

Dose Dependent Inhibition Induced by 4-Thiouridine

A dose dependent inhibition has been observed. In a previous test it was noted that 4-thiouridine inhibits neutrophil adhesion to activated HUVEC. The dose response now found may be explained by the fact that neutrophils are isolated from blood donors only.

Potency of Lead Compounds

Based on data from the above experiments, the following order can be proposed 4-thiouridine>isomaltitol>uridine.

Major inflammatory conditions where the present compounds find use is in asthmatic conditions. Crohn's disease, ulcerous colitis, reperfusion injury, auto-immune diseases, inflammatory bowel disease (IBD), arteriosclerosis, restenosis, cancer, coronary heart disease, diabetes, cancer metastasis, rheumatoidal diseases, dermatological diseases, such as psoriasis, seborrhea, burn injury, graft rejection.

The compounds of the present invention can be administered in the form of oral, rectal, injection, or inhalatory preparations. Oral compositions normally exist as tablets, granules, capsules (soft or hard), or powders, either coated or uncoated products. As coated products they may be merely enteric coated to provide for a more readily administered preparation, or as a sustained release coated composition, where the release of active compound will take place due to the dissolution of the coating, which dissolution is dependent on where in the gastro-intestinal tract one will have a release. Thus the release can be controlled as to place and time. It may also be advantageous to coat the active compound if this is subject to degradation, such as by gastric acid, in order then to have the compound to pass the stomach.

Tablets and capsules normally contain one dose of the active compound, i.e., the dose determined to fulfill the requirements of obtaining a therapeutically active level in serum or otherwise, either this is required once, twice or more times a day (24 hrs).

Rectal compositions are normally prepared as suppositories, where the active compound is dissolved or dispersed in a waxy compound or fat having a melting temperature in the range of the body temperature, as to release the active compound when administered rectally.

Preparations for injection are commonly made for subcutaneous, intramuscular, intravenous, or intra peritoneal administration. Injection solutions are normally provided with an adjuvant to facilitate absorption of the active compound.

Preparations for inhalation are commonly present as powders which are administered either in pressurized containers with a dosing nozzle, or in an inhaler system where the powder is dosed in the system and then the patient is inhaling air through the apparatus to such degree that the powder becomes airborne and enters the respiratory tract, including the lungs. Inhalation preparation are normally used for inflammatory conditions in the respiratory tract including the lungs.

The compositions contain 0.5 to 99% by weight of active compound, and the remainder is different inert, non-therapeutically active compounds which facilitate administration, preparation such as granulation, tableting, or storage. Such inert materials may, however, have a administratively positive effect.

The active compounds of the invention are administered in an amount of 1 to 100 mg per kilogram body weight depending on the condition of the patient, route of administration, age and body weight of the patient, and other considerations made by the physician. The most important aspect hereby is the serum concentration which may be 0.1 to 100 mM of active compounds, in accordance with the present findings.

FIGURE LEGENDS

FIG. 1 to 3 Adhesion of granulocytes to E-selectin transfected L-cells incubated with different concentrations of uridine, isomaltitol, and 4-thiouridine, respectively.

FIG. 4 to 6 Adhesion of Colo 201 to E-selectin transfected L-cells incubated with different concentrations of uridine, isomaltitol, and 4-thiouridine, respectively.

FIG. 7 to 9 Adhesion of granulocytes to TNF stimulated HUVEC co-incubated with different concentrations of isomaltitol, 4-thiouridine, and uridine, respectively FIG. 10 Expression of E-selectin on stimulated HUVEC co-incubated with different concentrations of 4-thiouridine.

The invention claimed is:

1. A method for treatment of acute or chronic inflammations, wherein a therapeutically effective amount of one or more of the compounds of the group consisting of 4-thiouridine and isomaltitol, is administered to a subject in need of such treatment wherein said acute or chronic inflammations are selected from the group consisting of asthma, Crohn's disease, ulcerative colitis, inflammatory bowel disease (IBD) and rheumatoidal arthritis.

2. The method according to claim 1, wherein the therapeutically effective compound is administered in such an amount that the serum concentration thereof is 0.1 to 100 mM.

3. A method for treatment according to claim 1, wherein the therapeutically effective compound is 4-thiouridine.

4. A method for treatment according to claim 1, wherein the therapeutically effective compound is isomaltitol.

* * * * *